United States Patent [19]
Slemker et al.

[11] Patent Number: 5,980,803
[45] Date of Patent: Nov. 9, 1999

[54] METHOD FOR CONSTRUCTING A PROSTHETIC LIMB SOCKET

[75] Inventors: Tracy Slemker, Clayton; Scott Schall, Englewood, both of Ohio

[73] Assignee: Prosthetic Design, Inc., Clayton, Ohio

[21] Appl. No.: 08/929,288

[22] Filed: Sep. 8, 1997

Related U.S. Application Data

[60] Provisional application No. 60/029,457, Oct. 30, 1996.

[51] Int. Cl.[6] .............................. B29C 33/44; B28B 7/10; B28B 13/06
[52] U.S. Cl. .............................. 264/222; 264/334; 425/2; 425/438; 601/901
[58] Field of Search ...................................... 264/222, 334; 425/2, 438; 623/33–38, 27; 601/901

[56] References Cited

U.S. PATENT DOCUMENTS

| | | | |
|---|---|---|---|
| 1,843,983 | 2/1932 | Lawrence | 425/2 |
| 3,377,416 | 4/1968 | Kandel | 264/222 |
| 5,503,543 | 4/1996 | Laghi | 425/2 |
| 5,718,925 | 2/1998 | Kristinsson et al. | 425/2 |

*Primary Examiner*—Jill L. Heitbrink
*Assistant Examiner*—Suzanne E. Mason
*Attorney, Agent, or Firm*—Thompson Hine & Flory LLP

[57] ABSTRACT

The present invention provides a method and apparatus for constructing a prosthetic limb socket. The method involves the steps of: a) creating a positive cast of a patient's residual limb; b) positioning a mechanical press on a distal end of the positive cast; c) molding a prosthetic socket component over the positive cast and over the mechanical press; and d) activating the mechanical press such that the prosthetic socket component is pushed apart from the distal end of the positive cast. Preferably, the mechanical press includes a spacer component adapted to abut a distal surface of the positive cast, a pusher component adapted to abut a proximate surface of a socket component formed over the positive cast, and an actuator for moving the pusher component from the spacer component. Thus, the method preferably also involves the step of activating the actuator to move the pusher component from the spacer component.

9 Claims, 8 Drawing Sheets

METHOD FOR CONSTRUCTING A PROSTHETIC LIMB SOCKET

CROSS REFERENCE TO RELATED APPLICATIONS

This application claims priority under 35 U.S.C. §119 from Provisional Application Ser. No. 60/029,457, filed Oct. 30, 1996.

BACKGROUND

The present invention relates to a method and apparatus for constructing a prosthetic limb socket, and more particularly, to an efficient and consistent method and apparatus for removing a positive cast of a patient's residual limb from within a molded prosthetic limb socket interface after the socket has been molded or laminated over the positive cast.

A prosthesis is often used to replace an amputated portion of a limb and to help restore the amputee's ability to use that limb. A prosthesis for a lower extremity amputation will often include an artificial foot connected to an upright assembly (pylon, tube or shaft) which is in turn connected to a custom fitted socket assembly. If the amputation is above the knee, the upright assembly will commonly also include an artificial knee joint.

The socket assembly of an above the knee prosthesis typically requires two inter-laying sockets: (a) an inner socket consisting of a flexible, thermoplastic or silicone material; and (b) a stronger, less flexible outer socket which is typically formed from a hard thermoplastic or PVC material. The two inter-laying sockets are attached to the upright assembly of the prosthesis. The inner socket is typically designed to interface with and cushion the amputee's residual limb, to protect the amputee's residual limb from the inter-connection components which attach the socket assembly to the upright assembly, and to provide an air tight seal between the residual limb and outer socket. The outer socket is adapted to be coupled to the upright assembly, and provides support to for the patient's residual limb.

The outer sockets are typically created by heating a thermoplastic "preform" cone until it is sufficiently soft and flexible, stretching the heated cone over a positive cast of the amputee's residual limb, and then vacuum forming the cone in place over the positive cast. Alternatively, the outer socket can be fabricated by heating an extruded sheet of thermoplastic material and wrapping the sheet over the positive cast; or by a laminating process using a fiber reinforced, thermal set plastic. It may be desirable to also permanently mold inter-connection components for coupling the outer socket to the upright assembly of the prosthesis into the outer socket during the vacuum forming operation. The inner sockets may also be created by heating a conventional preform cone and by stretching the preform cone over the positive cast of the amputee's residual limb.

Preform cones are typically formed from a clear thermoplastic material, a polypropylene polymer material, a polypropylene homopolymer material, or a flexible thermoplastic material, and are commercially available through Prosthetic Design, Inc., of Clayton, Ohio. Further, a socket manufacturing unit ("SMU"), which is also commercially available through Prosthetic Design, Inc., can be used to heat and mold the preform cones over the positive cast of the residual limb.

Positive casts of the amputee's residual limb are traditionally constructed by taking an impression or negative wrap of the amputee's residual limb, filling the negative impression with a mixture of plaster of Paris, corn starch, vermiculite and water. Once cured, the negative is stripped away and a positive model replica of the patient's residual limb remains. The positive cast is then modified to provide an optimal fit of what will become the prosthetic socket. By adding material or plaster in certain regions of the positive cast a void will be created in the socket which will act to relieve pressure in that area of the patient's residual limb. Likewise, by removing plaster in certain regions of the positive cast, more pressure will be applied to the patients residual limb in that area of the socket interface.

Once the socket material is cured over the positive cast as described above, the positive cast must be removed from the socket interface. Traditionally, the positive cast is chiseled or chipped out using screwdrivers, impact hammers, chisels, etc., until only the socket interface remains. The inter-connection components, the upright assembly and artificial foot are then attached, the prosthesis is aligned unique to each patient, and a prosthetic limb is the result.

Recently, the creation of the positive cast of a patient's residual limb has been performed using computer aided design and manufacturing (CAD/CAM) equipment and software. Such a process usually consists of digitizing a negative impression of the amputee's residual limb, modifying the digitized model of the amputee's residual limb using a CAD software package and then milling the positive cast of the modified digital model on a computer numerically controlled (CNC) machine (otherwise known as milling machines or carvers).

The CNC machine carves the modified positive cast from a "blank" of positive cast material which is commercially available in various materials, sizes and shapes. The majority of present day prosthesis facilities which utilize a CAD/CAM utilize blanks constructed from a formulation of plaster of Paris, corn starch, bleach, water and vermiculite to create their own blanks. Other facilities who utilize a CAD/CAM operation use blanks formulated from a urethane foam formulation.

The positive casts milled from a urethane blank must also be removed from the molded sockets or sleeves. Typically, it is known to remove the urethane positive casts from the sockets by chiseling out the positive cast using screwdrivers, impact hammers, rubber mallets, and chisels (similar to the tools used to remove the plaster casts). It is known to grind the foam casts out using a motorized grinding tool. However, these extraction method tend to be extremely messy and the fine material that is ground or chiseled from the positive casts tends to irritate the skin and respiratory system. Furthermore, the grinding tools have the propensity to scar the inside surface of the socket. It is also known to force the foam casts out utilizing a compressed air method. The compressed air method is preformed by first drilling a small hole in the distal end of the socket and inserting a tube into the hole and forcing compressed air through the tube and into the hole in an effort to force the foam blank out of the socket. A disadvantage with this removal method is if the plastic of the socket is still warm, it will deform to allow the foam blank to be pushed out, therefore the final plastic will not truly represent the positive model. An additional drawback is that the pressure being exerted may be extremely high and dangerous.

Accordingly, a need exists for constructing a prosthetic socket component which facilitates an efficient and consistent method for removing the positive cast of the wearer's residual limb from the socket component after the socket component has been molded over the positive cast.

SUMMARY OF THE INVENTION

The present invention provides a method and apparatus for constructing a prosthetic limb socket. The method comprises the steps of: a) creating a positive cast of a patient's residual limb; b) positioning a mechanical press on a distal end of the positive cast; c) molding a prosthetic socket component over the positive cast and over the mechanical press; and d) activating the mechanical press such that the prosthetic socket component is pushed apart from the distal end of the positive cast.

Preferably, the mechanical press comprises a spacer component adapted to abut a distal surface of the positive cast, a pusher component adapted to abut a proximate surface of a socket component formed over the positive cast, and an actuator for moving the pusher component from the spacer component. Thus, the above method preferably includes the step of activating the actuator to move the pusher component from the spacer component.

Further, the pusher component preferably includes a threaded bore extending therethrough and opening onto a distal surface of the spacer component and the actuator is a threaded bolt sized for being threaded into the threaded bore. Accordingly, the above method further includes the step of turning the threaded bolt within the threaded bore beyond a point where the threaded bolt contacts the distal surface of the spacer component, so that further turning of the threaded bolt within the threaded bore caused the pusher component to be forced away from the spacer component.

BRIEF DESCRIPTION OF THE DRAWINGS

FIG. 4B' is a perspective, distal view of a pusher component of the present invention;

DETAILED DESCRIPTION

Figure 1:
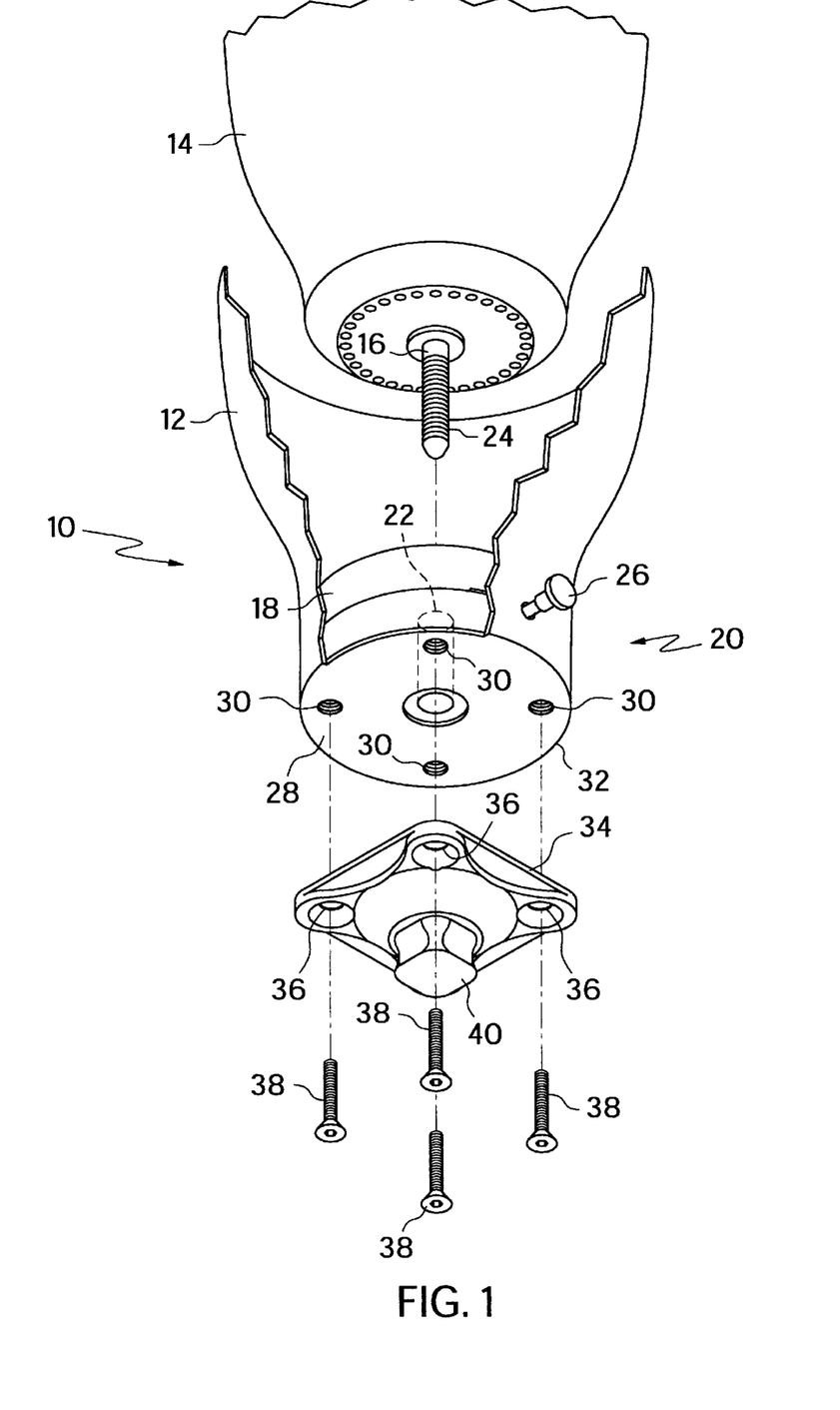
FIG. 1 is a perspective, exploded view of a prosthetic limb inner socket, outer socket and associated inter-connection components.

As shown in FIG. 1 the typical socket assembly will consist of a hard plastic outer socket 12 and a soft, resilient inner sleeve 14. The inner sleeve is formed to snugly fit over the residual limb of the patient, and to provide comfort to the residual limb of the patient when the prosthetic limb is worn by the patient. The inner sleeve 14 has a locking pin 16 formed integrally therewith and extending from the distal end of the sleeve. The locking pin 16 is adapted to engage with and lock within a universal lock 18 releasably positioned within an extended portion 20 of the outer socket 12. The universal lock 18 includes a channel 22 extending axially therethrough for receiving the locking pin 16. Spring-loaded projection(s) (not shown) within the channel 22 engage with the teeth 24 of the locking pin such that the projections and the shape of the teeth 24 allow the locking pin to be easily inserted within the channel 22 yet prohibit the locking pin from being extracted again from the channel 22. Accordingly, a spring-loaded release mechanism 26 may be pressed by the patient to disengage the projections within the channel 22 from the teeth, thereby allowing the locking pin 16 to be extracted again from the channel 22.

The distal end 28 of the universal lock 18 has four threaded holes 30 which are aligned with four holes extending through the distal end 32 of the outer socket. A titanium pyramid plate 34 includes four holes 36 which are to be aligned with the four threaded holes 30 of the universal lock 18. Accordingly, four threaded screws 38 are used to attach the pyramid plate 34 to the distal end 32 of the outer socket and simultaneously secure the universal lock 18 within the extended portion 20 of the outer socket. A pyramid part 40 formed integrally with the pyramid plate 34 is provided to attach the upright assembly (not shown) of the prosthetic limb to the distal end of the prosthetic limb socket assembly 10.

Figure 2:
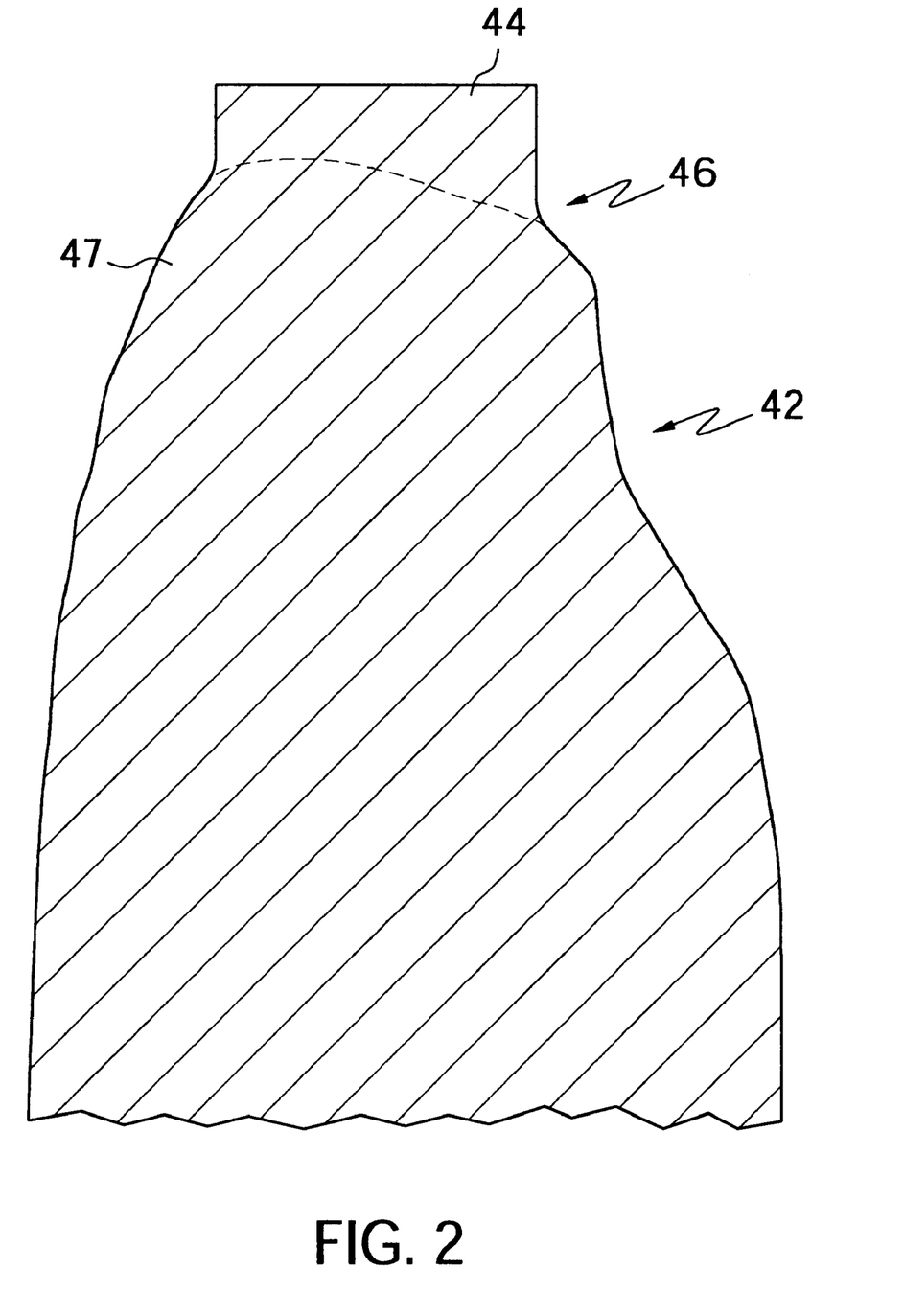
FIG. 2 is an elevational, cross-sectional view of a positive cast a patient's residual limb that includes extended dimensions of an inter-connection component attached thereto.

Construction of the outer socket 12 utilizing the method and devices of present invention will now be described in detail. As shown in FIG. 2, a positive cast of the patient's residual limb 42 is first fabricated and prepared by one of many methods and materials as known to one of ordinary skill in the art. Preferably, the positive cast will have cylindrical extended portion 44 extending from the distal end 46 of the limb portion 47 of the positive cast which provides the extended portion 20 of the outer socket 12. The extended portion 20 of the outer socket provides a space for the universal lock 18 therewithin; therefore, the cylindrical extended portion will typically have similar dimensions as the universal lock. As will described below, the extended portion 44 is several millimeters shorter than the extended portion 20 of the outer socket 12 because mechanical press components will be positioned on the extended portion 44 prior to molding the socket over the positive cast.

Figure 3:
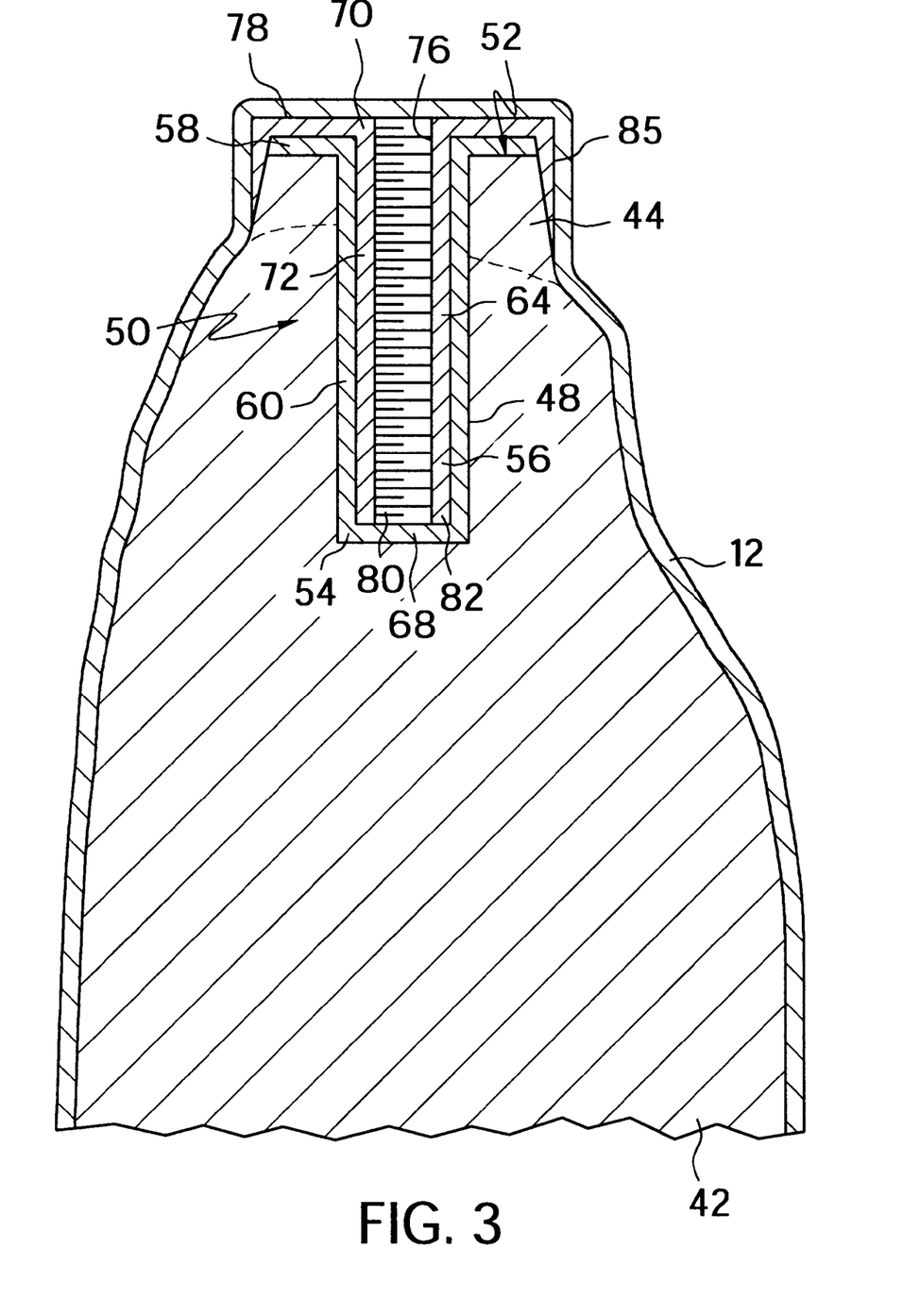
FIG. 3 is an elevational, cross-sectional view of a mechanical press of the present invention mounted onto the positive cast of FIG. 2 and having a socket molded thereover.

As shown in FIG. 3, a hole 48 is drilled into the distal end 52 of the positive cast. A mechanical press 50 is then inserted into the hole 48 and having an expanding portion positioned against the distal end 52 of the positive cast. Next, the heated PVC plastic socket material is then stretched and molded over the positive cast 42 and mechanical press 50 to form the socket 12. It should be apparent to one of ordinary skill in the art that, while the outer socket is described as being molded from a heated PVC material, the present invention is for use with any type of prosthetic limb socket material (soft or hard) known to those of ordinary skill in the art.

Figure 4A:
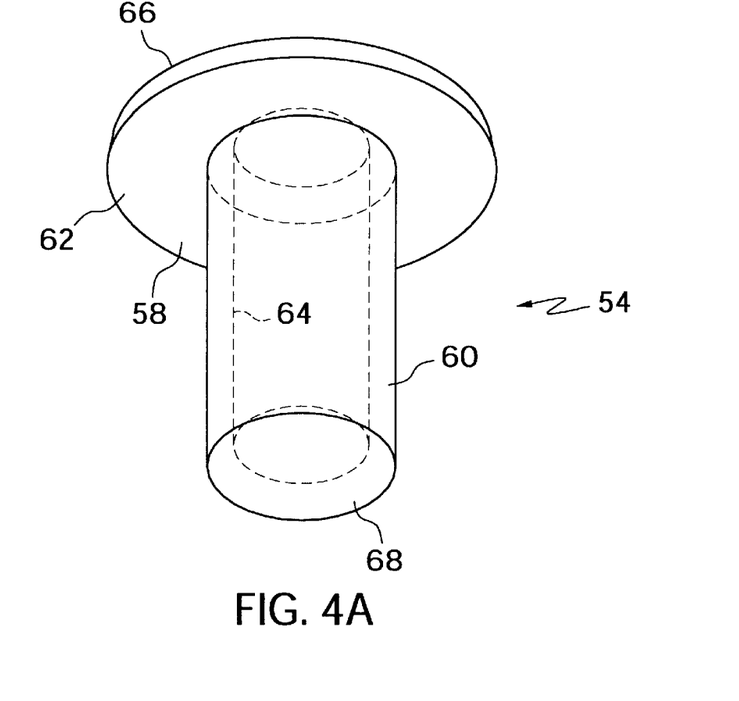
FIG. 4A is a perspective, proximate view of a spacer component of the present invention.
Figure 4B:
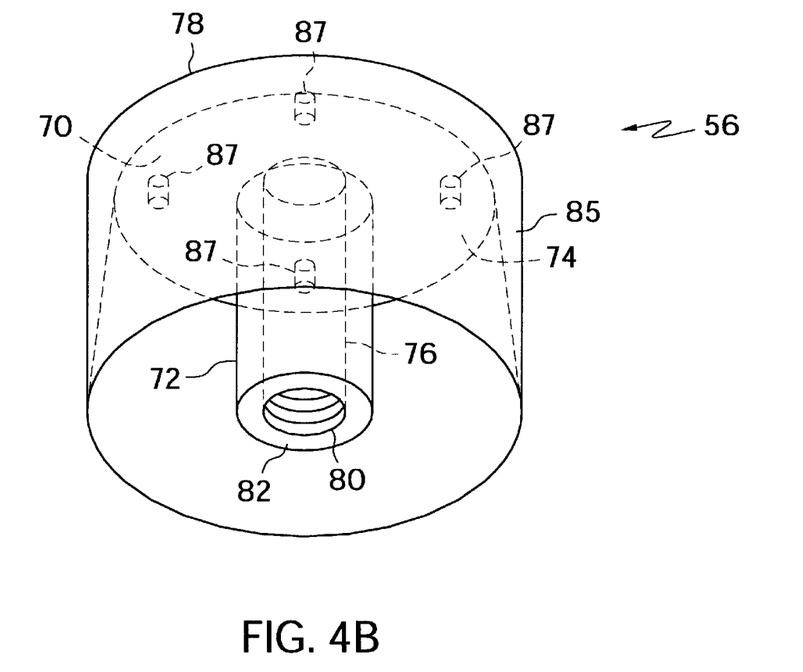
FIG. 4B is a perspective, proximate view of a pusher component of the present invention.

As shown in FIGS. 3, 4A, and 4B, the mechanical press components inserted in the hole 48 of the positive cast comprise a stationary or "spacer" component 54 and a mobile or "pusher" component 56. The spacer component includes a disk-shaped spacer plate 58 having a spacer tube 60 extending axially from the proximate surface 62 of the spacer plate 58. A channel 64 extends through the distal surface 66 of the spacer plate and extends through the spacer tube 60 ending at the cap 68 of the stationary tube 60. Preferably, the channel 64 extends along the axis of the spacer tube.

As shown in FIG. 4B, the pusher component 56 of the mechanical press assembly comprises a disk-shaped pusher plate 70 having a hollow sliding tube 72 extending axially from the proximate surface 74 of the pusher plate. A hole 76 extends through the distal surface 78 of the pusher plate, along the axis of the pusher plate, extends into the sliding tube 72, and opens at a mouth 80 in proximate surface 82 of the sliding tube 72. The interior surface of the hole 76 is threaded to receive the threaded drive bolt 84 (see FIGS. 4C and 5), which acts as the actuator component. The outer diameter of the sliding tube is preferably slightly less than the inner diameter of the channel 64 extending through the spacer tube 60 so that the sliding tube 72 can be slidably received in the channel 64. The pusher component 56 also preferably includes a tapered annular flange 85 extending downward from the proximate surface 74, along the circumferential periphery of the pusher plate 70, and is adapted to surround the outer circumference of the spacer plate 58 and lie below the surface of the distal end 52 of the positive cast. Therefore, the flange 85 acts to prevent the softened or liquid plastic from entering in-between the pusher plate 70 and the spacer plate 58 and in-between the spacer plate 58 and the distal end 52 of the positive cast during the socket molding operation, and also prevents any radial distortion in the extended portion 44 of the socket. The tapered inner surface of the flange 85 also allows for easier separation between the pusher plate 70 and the spacer plate 58. At this point it should be apparent to those of ordinary skill in the art that in an alternate embodiment, the spacer component 54 may instead have a flange, similar to flange 85, extending upwardly and surrounding the periphery of the pusher plate 70.

As shown is FIG. 4B' the distal surface 78 of the pusher plate 70 has four projections or conical spikes 86 extending therefrom. Therefore, when the outer socket 12 is molded over the distal surface 78 of the pusher plate (as shown in FIG. 3) the four conical spikes 86 will form four indentations within the distal end of the socket. Preferably these indentations are located to align a drill bit prior to the drilling of the holes through the distal end of the socket. Such socket holes are preferably aligned with the holes 30 and 36 of the universal lock 18 and pyramid plate 34, respectively. The pusher plate 70 also preferably includes several small diameter holes 87 extending therethrough to allow air paths to form during separation and to prevent the formation of a vacuum between the pusher plate and spacer plate. Such holes 87 are preferably 1/56 inches in diameter.

As is further shown in FIG. 3 the combination of the thickness of the spacer plate 58 and the pusher plate 70 provide the additional length for the cylindrical extended portion 44 of the positive cast for providing the extended portion 20 of the socket 12; and the outer diameter of the pusher plate 70 is preferably equal to the outer diameter of the universal lock 18, which is to be received into the extended portion 20 of the socket 12.

Figure 4C:
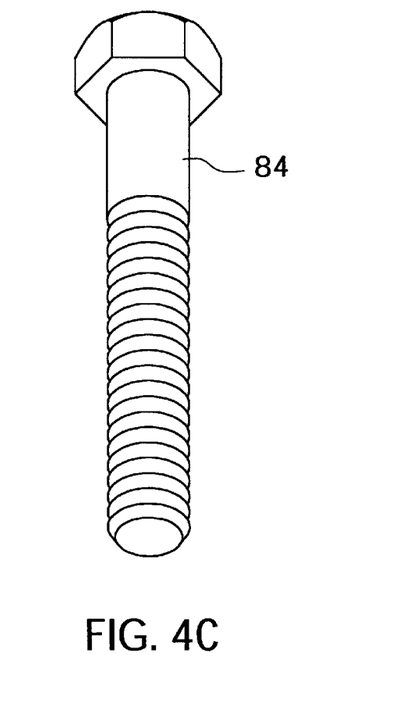
FIG. 4C is a perspective view of an actuator component of the present invention.
Figure 5:
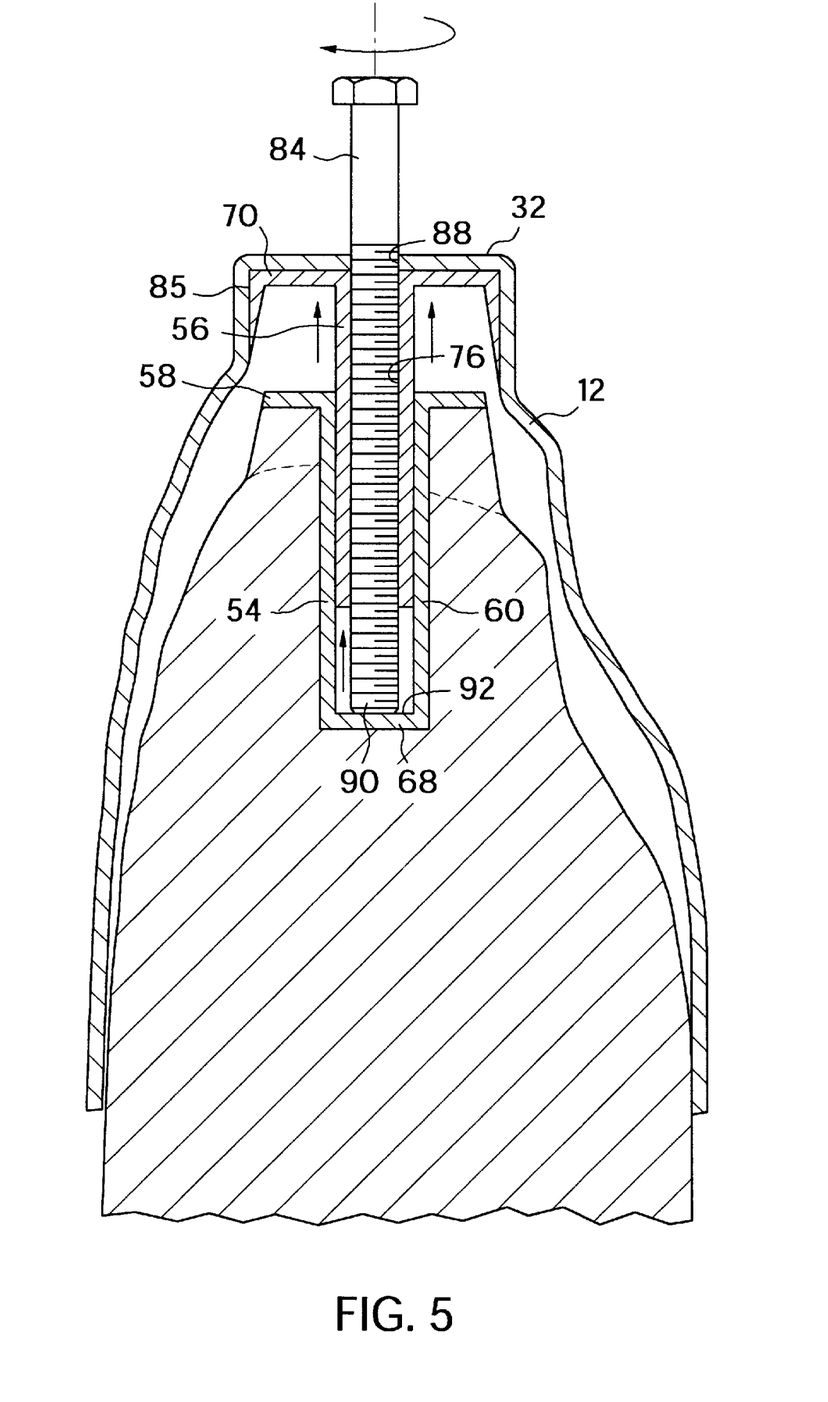
FIG. 5 is the view of FIG. 3, depicting the mechanical press being activated.

As shown in FIGS. 4C and 5, the last component of the mechanical press is a threaded drive bolt 84, sized to be screwed into the threaded hole 76.

Referring to FIG. 5 the procedure for constructing the outer socket continues as follows: first a hole 88 is drilled through the distal surface of the outer socket 12; next, the threaded bolt 84 is screwed through the hole 88 and into the threaded hole 76 of the pusher component 56 and is screwed continuously until the end of the bolt 90 abuts the distal surface 92 of the cap 68 of the spacer tube 60; thereafter, additional screwing of the drive bolt 84 will force the pusher component 56 away from the spacer component 54, and in turn, will force the pusher plate 70 away from the spacer plate 58, causing the positive cast 42 to be separated from the outer socket 12.

By using the mechanical press components of the present invention in the construction of the outer socket 12, the positive cast 42 may be easily removed from the molded socket 12 without having to chisel or grind the positive cast from the socket and without having to eject the positive cast from the socket using pressurized air.

It will be apparent to those of ordinary skill in the art that while the mechanical press of the present invention is preferably a screw-jack type component as described above, other types of mechanical press components, which can positioned over the distal end of the positive cast prior to molding the socket over the positive cast, can be utilized with equal satisfactory results. For example, the use of a pneumatically controlled or hydraulically controlled press; or a motorized press will fall within the scope of the present invention.

Furthermore, it will also be apparent to those of ordinary skill in the art that pusher plates and spacer plates of different geometries and sizes can also be used depending upon the ultimate required shape of the inner surface of the socket's distal end. For example, if the inner surface of the socket's distal end required a "bowl" shape, the pusher plates and the spacer plates would correspondingly be substantially dome shaped. Further, if necessary, the pusher plates and spacer plates could be square or some other shape; or the pusher plates and spacer plates could have equal diameters.

Because a low profile universal lock 18 is utilized in the preferred embodiment; it is advantageous to have a completely flat inner distal surface of the final molded socket, which is parallel to the completely flat outer distal surface of the final molded product. These parallel surfaces help prevent the screws 38 from breaking during use of the prosthetic limb and help prevent cold-flow damage of the socket 12. Therefore, the flat distal surface 78 of the pusher plate facilitates in providing a flat inner distal surface of the prosthetic limb socket 12.

Figure 6:
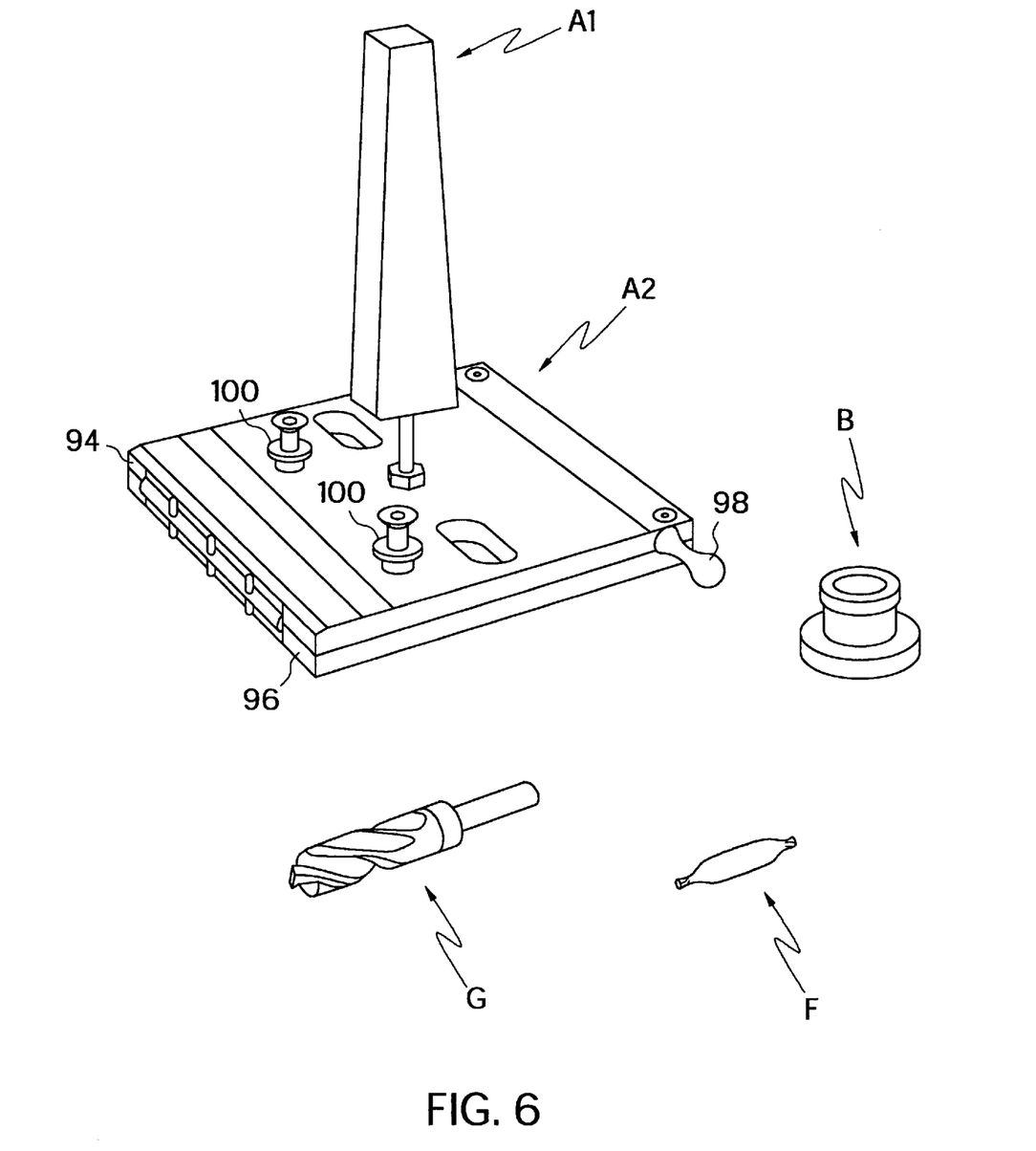
FIG. 6 is a perspective view of tooling components for use with the present invention.

The preferred embodiment of the apparatus for extracting a urethane foam positive cast from the socket molded thereon utilizes the components as shown in FIG. 6. The urethane foam positive cast is milled from a urethane foam blank as discussed above. The component designated as A1 is a mandrel for mounting the urethane foam positive cast to a drill press after it has been milled in the CNC milling machine. Each of the urethane foam blanks have a cavity extending into their proximate ends for facilitating the mounting of the blank on a mandrel of a CNC milling machine. The mandrel A1 is preferably the exact shape as that of the CNC milling machine mandrel; therefore, the positive cast milled from the foam urethane blank will mount on the mandrel A1. The mandrel is attached to a locating fixture A2 which includes two aluminum plates, a top plate 94 hinged at one edge to a bottom plate 96, and slotted to allow access to the mounting hardware. A handle 98 mounted to the top plate 94 allows the top plate to be pivoted up from the bottom plate, thus providing operator access to the mandrel when the fixture A2 is mounted on a drill press. The two aluminum plates are also tapped in the center to allow the mandrel A1 to be mounted thereon.

Figure 7:
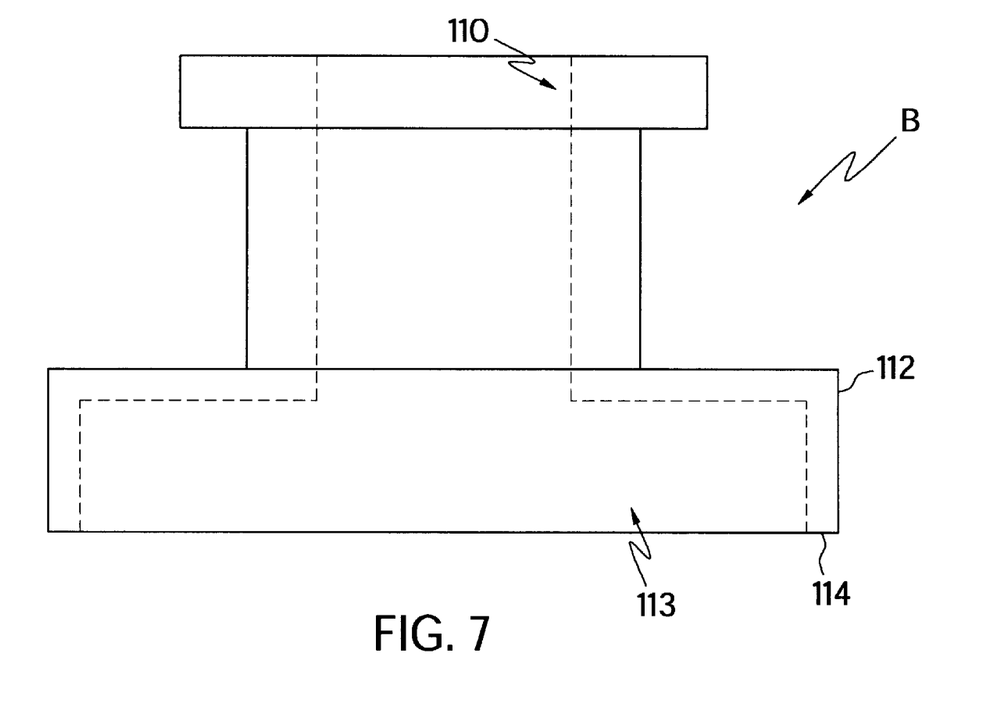
FIG. 7 is an elevational, side view of a drill guide component for use with the present invention.

The locating die component designated as B, a side view of which is depicted in FIG. 7, has a 1 1/16 inch inside diameter through-hole 110. The base 112 of the die has an inside diameter cavity 113 extending from the bottom surface 114 of the die. The cavity 113 has a 65 millimeter inside diameter which is adapted to rest on the cylindrical extended portion 44 extending from the distal end 46 of the positive cast (see FIG. 2). The through-hole 110 is adapted to guide a drill bit G to the center of the distal end of the positive cast such that the drill bit G can drill the hole 48 into the distal end of the positive cast (see FIG. 3). The drill bit G is preferably a 1 1/16 inch diameter bit. Additionally, the cavity 113 is preferably approximately three-eighths of an inch deep.

Preferably the spacer component 54 has a spacer plate 58 with a diameter of approximately 63 millimeters and a thickness of approximately 3 millimeters. The spacer tube 60 preferably has an outside diameter of 1 1/16 inches and an inside smooth diameter of 27/32 of an inch. The pusher component has a disc-shaped pusher plate 70 with an outer diameter of 65 millimeters and a thickness of approximately 3 millimeters, and the sliding tube 72 has an outside diameter of 13/16 of an inch and a 1/2"×20 tapped bore extending through the axis of the tube. The top surface of the pusher plate 70 has four conical spikes 86, each having a base diameter of 6 millimeters and a height of 2.5 millimeters, arranged at a standard European prosthetic four-hole pattern.

The drive bolt 84 is a steel 1/2×20 standard bolt, 8 inches long, with a 1/2"×20 nut welded on one end. The nut ("hex-head") requires a 3/4 inch socket. Equipment set-up is as follows:

A standard drill press is necessary with enough height allowance for the socket and the drill bit G combined. The locating fixtures A1 and A2 should be mounted onto the drill press working table. The working table should have height and rotation adjustments as well as a tool cut depth (the maximum distance that you can bring the cutting tool down from its home position) of at least 5 1/2 inches. Also, an electric, battery powered or pneumatic torque limit hand drill with a socket driver and a 3/4 inch socket is recommended to turn the drive bolt 84.

As discussed above, the positive cast of the residual limb preferably has a 65 millimeter diameter cylindrical extension 44 extending from the distal end 46 of the limb portion 47 of the positive cast. Preferably the cylindrical extension 44 has a thickness, or height of 13 millimeters. The addition of this cylindrical extension can be accomplished with tools available in a cad or traditionally by using a fabrication plate molded directly onto the positive cast of the residual limb.

To drill the hole 48 through the distal end of the positive cast, the positive cast is first placed onto the mandrel A1 by tilting the top plate 94 of the locating fixture base A2 using the handle 98. The drill bit G is then clamped into the drill press head assembly. The locating die B is then placed onto the distal end of the positive cast, over the cylindrical extension 44. The working table of the drill press is then lifted such that the drill bit G is approximately 2 inches from the top of the locating die B. The height adjustment clamp is then locked on the drill press. The working table and the locating fixture A2 are then adjusted until the drill bit G is aligned with the through-hole 110 of the locating die B.

When the drill bit is aligned, the rotation adjustment clamps on the drill press are locked and the two bolt assemblies 100 on the locating fixture are tightened to lock the locating fixture in place. The locating die is then removed from the positive cast and the drill bit G is lowered until the tip contacts the distal end 52 of the positive cast. The tool cut depth of the drill press is adjusted to allow an additional 3 1/2 inch cutting depth. Once this is accomplished, the drill bit is allowed to return to the home position. The drill press is then turned on, and while holding the positive cast for stabilization, the drill bit G is lowered to bore the hole 48 into the distal end of the positive cast, 3 1/2 inches deep. The drill bit G is then returned to the home position, and the drill press is powered off. The positive cast is then removed from the mandrel A1 by tilting the top plate 94 of the locating fixture A2 by using the handle 98.

The spacer tube 60 of the spacer component 54 is next inserted into the hole 48 drilled into the distal end of the positive cast, and the sliding tube 72 of the pusher component 56 is inserted into the channel 64 of the stationary tube 60, ensuring that the four conical spikes 86 are aligned with the line of progression. Next, the plastic socket is then molded or laminated over the positive cast and over the mechanical press components inserted into the hole 48.

To remove the positive cast and the mechanical press components from the socket 12 which has been molded over the positive cast and press components, the combination bit F is inserted in place of the drill bit G in the drill press head assembly and the positive cast is placed onto the mandrel A1, as described above. The drill press is powered on and while holding the socket and positive cast for stabilization, the combination bit is lowered to bore a hole through the plastic or laminated distal end of the socket covering the positive cast. The combination bit is then returned to the home position and the drill is powered off. Next, the positive cast and socket are removed from the mandrel again, as described above.

The next step in removing the socket from the positive cast is to cut the trim line through the socket without cutting any of the positive cast material beneath. Next, the positive cast and the socket are placed in a standard vice or a holding fixture. After ensuring that the 1/2 inch center hole drilled into the distal end of the socket is free of any debris, the drive bolt 84 is lubricated and inserted through the threaded bore 76 of the sliding tube 72. The drive bolt 84 is then turned slowly until the end of the drive bolt comes into contact with the cap 68 of the stationary tube 60. Finally, the drive bolt is continued to turn until the positive cast is separated from the socket.

Having described the invention in detail and by reference to the drawings, it will be apparent that modification and variations are possible without departing from the scope of the invention as defined in the following claims.

What is claimed is:

1. A method for constructing a prosthetic limb socket comprising the steps of:

a) creating a positive cast of a patient's residual limb;

b) positioning a mechanical press on a distal end of the positive cast;

c) forming a prosthetic socket component over the mechanical press and over at least a portion of the positive cast; and d) after the prosthetic socket component has cured, activating the mechanical press such that the prosthetic socket component is pushed apart from the distal end of the positive cast, thereby facilitating removal of the positive cast from the prosthetic socket component.

2. The method of claim 1, wherein the mechanical press includes a spacer component abutting the positive cast and a pusher component abutting the prosthetic socket component, and the activating step includes a step of forcing the pusher component away from the spacer component.

3. The method of claim 2, wherein:

the pusher component includes a threaded bore extending therethrough and opening onto a distal surface of the spacer component;

the mechanical press includes a threaded bolt; and the forcing step includes a step of continuously turning the threaded bolt within the threaded bore.

4. A method for constructing a prosthetic limb socket comprising the steps of:

a) providing a positive cast of a patient's residual limb;

b) positioning a mechanical press on a distal end of the positive cast;

c) providing a preform cone of a thermoplastic material;

d) heating the preform cone;

e) stretching the heated preform cone over the mechanical press and at least a portion of the positive cast; and f) after the stretching step, removing the positive cast from the preform cone by activating the mechanical press.

5. The method of claim 4, wherein:

the step of positioning the mechanical press on the distal end of the positive cast includes the steps of positioning a spacer component of the mechanical press on the distal end of the positive cast and positioning a pusher component of the mechanical press on a distal end of the spacer component; and the step of activating the mechanical press involves the step of forcing the pusher component away from the spacer component.

6. The method of claim 5, wherein one of the pusher component and spacer component have an outer periphery matching an outer periphery of an inter-connection component adapted to be received within a distal end of the prosthetic limb socket so that the stretching step involves the step of providing space for the inter-connection component within the prosthetic limb socket.

7. A method for constructing a prosthetic limb socket comprising the steps of:

a) providing a positive cast of the prosthetic limb socket;

b) positioning a mechanical press on a distal end of the positive cast;

c) laminating a prosthetic limb socket over the mechanical press and at least a portion of the positive cast;

d) after the laminating step, allowing the prosthetic limb socket to cure; and e) after the step of allowing the prosthetic limb socket to cure, removing the positive cast from the prosthetic limb socket by activating the mechanical press.

8. The method of claim 7, wherein:

the step of positioning the mechanical press on the distal end of the positive cast includes the steps of positioning a spacer component of the mechanical press on the distal end of the positive cast and positioning a pusher component of the mechanical press on a distal end of the spacer component; and the step of activating the mechanical press involves the step of forcing the pusher component away from the spacer component.

9. The method of claim 8, wherein one of the pusher component and spacer component have an outer periphery matching an outer periphery of an inter-connection component adapted to be received within a distal end of the prosthetic limb socket so that the stretching step involves the step of providing space for the inter-connection component within the prosthetic limb socket.

* * * * *